US008790670B2

(12) United States Patent
Yarlagadda et al.

(10) Patent No.: US 8,790,670 B2
(45) Date of Patent: Jul. 29, 2014

(54) DETERGENT COMPOSITIONS DISPERSED IN PERSONAL CARE PRODUCTS COMPRISING A SORBENT CARRIER

(71) Applicant: The Dial Corporation, Scottsdale, AZ (US)

(72) Inventors: Travis T. Yarlagadda, Phoenix, AZ (US); Sarah Moore, Scottsdale, AZ (US); Tasha Zander, Phoenix, AZ (US); Elizabeth Nofen, Gilbert, AZ (US); Saiid Mohammed, Somerset, NJ (US); Gerald Decker, Aurora, IL (US); Matthew Romaine, Franklin Park, NJ (US); Chris Proulx, St. Piscataway, NJ (US); Chelsea Stanton, Point Pleasant, NJ (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

(21) Appl. No.: 13/730,708

(22) Filed: Dec. 28, 2012

(65) Prior Publication Data

US 2014/0186412 A1   Jul. 3, 2014

(51) Int. Cl.
*C11D 7/08* (2006.01)
*C11D 3/08* (2006.01)
*C11D 3/22* (2006.01)

(52) U.S. Cl.
USPC ........... 424/401; 510/119; 510/130; 510/253; 510/434; 510/470; 510/477; 510/511; 424/409; 424/65; 424/70.31

(58) Field of Classification Search
USPC ......... 510/119, 130, 253, 434, 470, 477, 511; 424/401, 409, 65, 70.31
See application file for complete search history.

(56) References Cited

U.S. PATENT DOCUMENTS

| 3,974,270 A | 8/1976 | Kenkare et al. |
| 4,749,508 A * | 6/1988 | Cockrell et al. .............. 510/201 |
| 5,336,665 A | 8/1994 | Garner-Gray et al. |
| 2003/0118520 A1 * | 6/2003 | Reinhardt et al. .............. 424/53 |
| 2005/0153862 A1 | 7/2005 | Lau et al. |
| 2011/0236493 A1 | 9/2011 | Canham et al. |
| 2013/0164236 A1 * | 6/2013 | Yarlagadda et al. ............ 424/65 |

FOREIGN PATENT DOCUMENTS

EP    0753571 A1    1/1997

OTHER PUBLICATIONS

PCT International Search Report (PCT/US2013/070971) dated Jan. 27, 2014.

* cited by examiner

*Primary Examiner* — Charles Boyer
(74) *Attorney, Agent, or Firm* — David K. Benson

(57) ABSTRACT

Detergent compositions and detergent compositions dispersed in personal care products are provided herein. In one embodiment, a detergent composition is provided and comprises a sorbent carrier. The detergent composition also includes a sorbed component including an acid and a surfactant. The sorbed component is sorbed by the sorbent carrier.

17 Claims, No Drawings

DETERGENT COMPOSITIONS DISPERSED IN PERSONAL CARE PRODUCTS COMPRISING A SORBENT CARRIER

TECHNICAL FIELD

The technical field relates generally to detergent compositions, detergent compositions dispersed in personal care products, and methods of making detergent compositions, and more particularly relates to detergent compositions in which detergent components are sorbed by a sorbent carrier.

BACKGROUND

Antiperspirant and deodorant compositions are well known personal care products used to prevent or eliminate perspiration and body odor caused by perspiration. The compositions come in a variety of forms and may be formulated, for example, into aerosols, pumps, sprays, liquids, roll-ons, lotions, creams, sticks, soft solids, and other products.

Various types of stick antiperspirant compositions are desired by a large majority of the population because of their ease of application and the presence of active antiperspirant compounds, e.g., antiperspirant salts, that prevent the secretion of perspiration and its accompanying odors. In one type, an antiperspirant salt is suspended in an anhydrous vehicle often including a solid water-insoluble wax.

Fabric staining on garments worn by antiperspirant users, particular in the underarm area, has long been a concern with antiperspirant use. There are various factors that are believed to cause fabric staining by antiperspirant use. First, the acidic nature of typical active antiperspirant compounds in combination with perspiration may cause a fabric yellowing reaction to occur over time due to repeated and prolonged exposure. A second factor may be the presence of iron in the antiperspirant composition, such as in the active antiperspirant compound, clay, and/or fragrance, which can transfer to the garment and oxidize. Another factor is the presence of iron, calcium, and/or other inorganic metals found in the water used to wash a garment previously worn by the antiperspirant user. These inorganic metals can inhibit complete removal of the antiperspirant ingredients, resulting in a buildup of antiperspirant on the garment after multiple wearings and washings, and/or the inorganic metals can precipitate onto the garment to cause fabric staining.

Heretofore, efforts to address fabric staining typically have included incorporating less active antiperspirant compound(s) into the antiperspirant composition. However, many of these reduced active antiperspirant compounds lack antiperspirant efficacy relative to higher concentration active antiperspirant compounds. Also, fabric staining caused by factors other than the active antiperspirant compound, e.g., presence of iron in the antiperspirant composition, inorganic metals present in the wash water, and antiperspirant buildup on the garment, are not addressed by simply using an antiperspirant composition with a less acidic active antiperspirant compound.

Accordingly, it is desirable to provide detergent compositions that can be dispersed in personal care products such as antiperspirants and deodorants. Further, it is desirable to provide detergent compositions that address fabric staining of garments worn by antiperspirant users. Also, it is desirable to provide detergent compositions that incorporate silica particles that are sorbed with detergent and are configured to release the detergent in a washing environment. Furthermore, other desirable features and characteristics will become apparent from the subsequent detailed description of the invention and the appended claims, taken in conjunction with this background.

BRIEF SUMMARY

Detergent compositions and detergent compositions for use in personal care products are provided herein. In an exemplary embodiment, a detergent composition is provided and comprises a sorbent carrier. The detergent composition also includes a sorbed component including an acid and a surfactant. The sorbed component is sorbed by the sorbent carrier.

In accordance with another exemplary embodiment, a detergent composition comprises an aqueous component including a phosphoric acid, an alpha hydroxy acid, and a surfactant. Further, the aqueous component has a pH less than about 1. The detergent composition also includes a sorbent carrier. The aqueous component is sorbed by the sorbent carrier.

In accordance with another exemplary embodiment, a detergent composition dispersed in a personal care product is provided. The detergent composition comprises an aqueous component including an acid and a surfactant. The detergent composition further includes a sorbent carrier comprising hydrophobic particles. Each particle has an inner portion and an outer coating, and the inner portion is less hydrophobic than the outer coating. The aqueous component is sorbed by the inner portion of the sorbent carrier.

DETAILED DESCRIPTION

The following detailed description is merely exemplary in nature and is not intended to limit the detergent compositions, detergent compositions dispersed in personal care products, and methods for making detergent compositions described herein. Furthermore, there is no intention to be bound by any expressed or implied theory presented in the preceding technical field, background or brief summary, or in the following detailed description. It is noted that while the detergent compositions are discussed in particular relation to antiperspirant or deodorant products, they are not so limited in their use and may be applied to other personal care products.

The various embodiments contemplated herein relate to detergent compositions and personal care products including dispersed detergent compositions. The detergent compositions include detergent components that are sorbed by a sorbent carrier. As used herein, "sorbed" means held, as by absorption into or adsorption onto, by another substance. The sorbent carrier is configured to dissolve in an alkaline environment, such as during laundry washing. When employed in personal care products, negative interactions between the detergent components and other portions of the personal care product are avoided. In a particular embodiment, the personal care product is an antiperspirant composition that exhibits strong antiperspirant efficacy. Certain embodiments herein involve detergent compositions that include a sorbed component including a phosphoric acid, an alpha hydroxy acid, an acid precursor, and a surfactant. Other embodiments provide a detergent composition including an aqueous component having a pH less than about 1 sorbed by the sorbent carrier. In other embodiments, the detergent composition dispersed in a personal care product includes a sorbent carrier comprising porous hydrophobic particles with inner portions that are less hydrophobic than outer coatings.

The detergent compositions are considered to be comprised of a sorbed component and a sorbent carrier. The sorbed component includes the detergent actives such as acidic detergent agents, builders and surfactants. The sorbent carrier is hydrophobic such that after sorbing the sorbed component, the sorbent carrier impedes contact between water and the sorbed component. The sorbent carrier is configured to dissolve in high pH environments, such as in a laundry washing environment. Upon even partial dissolution, the sorbed component may be released from the sorbent carrier into the washing environment. In the case of a detergent composition dispersed in a personal care product such as an antiperspirant or deodorant, the sorbed component is released on the clothing at the site where fabric staining is likely to be problematic.

Acids.

The sorbed component of an exemplary detergent includes acidic detergent agents or acids. Specifically, the exemplary detergent may include alpha hydroxy acids. Acidic detergent agents may be selected to support the detergent's surfactant action and to eliminate water hardness in the washing environment.

"Hydroxy acid" refers to a compound having a carboxylic acid functionality and a hydroxy functionality. Alpha-hydroxy acids consist of a mono- or polycarboxylic acid containing one or more hydroxyl functions, at least one of these hydroxyl functions necessarily occupying a position alpha to the acid (carbon adjacent to a carboxylic function). This acid may be present in the final detergent composition in free acid form. In certain embodiments, the alpha hydroxy acid is selected from linear or branched alpha hydroxy acids no more than 6 carbon atoms and aromatic alpha hydroxy acids. The detergent compositions may, of course, contain one or more alpha hydroxy acids. The alpha hydroxy acid may include, without limitation, gluconic acid, malic acid, citric acid, glycolic acid, lactic acid, mandelic acid, methyllactic acid, phenyllactic acid, tartronic acid, tartaric acid, benzylic acid, 2-hydroxycaprylic acid, salicylic acid, maleic acid, pyruvic acid and hydroxy-octanoic acid, and combinations thereof.

In an exemplary embodiment, the detergent composition includes a combination of gluconic acid, malic acid, and citric acid. For example, the detergent composition may include, by total weight percent (wt %) of the detergent composition, about 2 to about 10 wt % gluconic acid, about 10 to about 20 wt % malic acid, and about 20 to about 30 wt % citric acid. More generally, the detergent composition may include about 32 to about 60 wt % alpha hydroxy acid.

Alpha hydroxy acids may cause local irritation when applied to sensitive areas of the skin. Also, it is difficult to formulate compositions containing alpha hydroxy acids because of the desirability to formulate the composition at an acid pH at which the most efficacious free acid form of the alpha hydroxy acid will predominate. For skin wash compositions, this problem is exacerbated by the difficulty of obtaining a detergent base system at sufficiently low pH.

Herein, the detergent composition prevents irritation to skin by sorbing the detergent components, including alpha hydroxy acids, onto a sorbent carrier that inhibits contact between the alpha hydroxy acids and the skin. Further, the detergent composition is formulated at extremely acidic pH as discussed below, optimizing the presence of the free acid form of the alpha hydroxy acid.

Phosphoric acid may also be used in the detergent composition as an additional acidic detergent agent and/or as complexing or softening agents to reduce the hardness of the water in the washing environment. Water softeners remove $Ca^{2+}$ and $Mg^{2+}$ ions from "hard" water. If not removed, these hard-water ions react with soap and form insoluble deposits that cling to laundry and the washing machine. The phosphoric acid causes the $Ca^{2+}$ and $Mg^{2+}$ ions to form soluble chemical species, called complexes or chelates. These complexes prevent the $Ca^{2+}$ and $Mg^{2+}$ from reacting with soap and forming deposits.

In an exemplary embodiment, the detergent composition includes, by total weight percent (wt %) of the detergent composition, about 5 to about 15 wt % phosphoric acid. Phosphoric acid can be a skin irritant or even cause burns depending on the concentration and duration of contact. Therefore, sorbing the phosphoric acid onto a sorbent carrier may enable the use of phosphoric acid at high concentrations in personal care products without irritation or injury.

Other acids, such as those known for use in detergents, including nitric acid, sulfamic acid, hydrochloric acid, hydroxyacetic acid, may be included in the detergent composition disclosed herein. Typically, the total acid concentration of the detergent composition will be, by total weight percent (wt %) of the detergent composition, about 37 to about 65 wt %.

Acid Salts.

The sorbed component of an exemplary detergent composition may further include acid salts as a detergent builder or as a source for additional acidic detergent agent. More particularly, the detergent composition may contain water soluble acid salts, such as citric acid salts or citrates. For example, sodium citrates including monosodium citrate, or sodium dihydrogen citrate, may be used to reduce water hardness.

Acid salts may be included in order to provide for additional acidity when the sorbed component is released in the laundry washing environment. Specifically, the acid mixture of the sorbed component may drive the acid salt to acid. For example, sodium dihydrogen citrate may be driven to citric acid. As a result, the deliverable amount of citric acid to the targeted clothing area may be higher than the amount of citric acid in the sorbed component. This increased amount is delivered without increasing any skin irritation caused by citric acid.

In an exemplary embodiment, the detergent composition includes, by total weight percent (wt %) of the detergent composition, about 0.1 to about 15 wt % citrate, and more specifically, sodium dihydrogen citrate.

Surfactant.

The sorbed component of the exemplary detergent composition also includes at least one surfactant. A surfactant is a compound that lowers the surface tension of a liquid or the interfacial tension between two liquids or between a liquid and a solid. When added to water for laundering, a surfactant significantly reduces the surface tension of the water, allowing the water to penetrate the fabric rather than slide off its surface. The result is that the water can function more effectively, acting to loosen the dirt from the clothing, and then hold it until it can be washed away.

Surfactants have a hydrophobic end and a hydrophilic end. The hydrophobic end consists of an uncharged carbohydrate group that can be straight, branched, cyclic or aromatic. Depending on the nature of the hydrophilic part the surfactants are classified as anionic, nonionic, cationic or amphoteric. Anionic surfactants have a hydrophilic end that consists of a negatively charged group like a sulfonate, sulfate or carboxylate, and are sensitive to water hardness. Nonionic surfactants include a non-charged hydrophilic part, e.g. an ethoxylate. Nonionic surfactants are not sensitive to water hardness. Cationic surfactants have a hydrophilic end that contains a positively-charged ion. Amphoteric surfactants or Zwitterionic surfactants have both cationic and anionic centers attached to the same molecule.

In an exemplary embodiment, a nonionic surfactant is included in the sorbed component of the detergent composition. Nonionic surfactants are well known include many suitable compounds for use in the detergent composition. In one embodiment, the nonionic surfactant may be caprylyl/capryl glucoside (octyl/decyl glucoside or C8-10 alkyl polyglucoside) which is a glucose alkyl ether with a pH of 5.5 to 6. In an exemplary embodiment, the detergent composition includes, by total weight percent (wt %) of the detergent composition, about 5 to about 15 wt % surfactant, and more specifically, a nonionic surfactant such as caprylyl/capryl glucoside.

Water.

In exemplary embodiments, the sorbed component of the detergent compositions is aqueous. In an exemplary embodiment, the detergent composition includes, by total weight percent (wt %) of the detergent composition, about 5 to about 25 wt % water, optimized to allow for a maximum concentration of active (acid/surfactant) in water solution.

In an exemplary embodiment, the water is provided to solubilize and concentrate the acid in liquid form. During formation of the sorbed component of the detergent composition, the acid, surfactant, acid salt (if included) and water are provided in concentrations to concentrate the acid level (i.e., minimize pH). In an exemplary embodiment, the pH of the sorbed component is less than about 3.5, for example less than about 2, such as less than about 1.5, for example less than about 1.

Sorbent Carrier.

Sorbing the aqueous detergent component with a sorbent carrier allows the aqueous detergent component to be held for release from the sorbent carrier upon introduction to a selected environment to remove or inhibit formation of a fabric stain. For example, the sorbent carrier may be configured to dissolve in an alkaline environment having, for example, a pH of at least 8, of at least 9, or of at least 10, such as at least about 11. Typical laundry detergent provides such an alkaline environment during washing. Therefore, the aqueous detergent component may be held by the sorbent carrier until it is at least partially dissolved in the mixture of water and laundry detergent in a washing machine. Upon partial dissolution of the sorbent carrier, the aqueous detergent component is released on the garment, and may remove or inhibit formation of a stain on the garment.

The sorbent carrier may comprise porous and/or nonporous particles. An exemplary sorbent carrier includes hydrophobic silica particles. "Hydrophobic" silica particles, as the term is used herein, encompasses silica particles having varying levels or degrees of hydrophobicity. The degree of hydrophobicity imparted to the silica particles will vary depending upon the type and amount of treating agent used.

Preferably, hydrophobic silica particles are formed from treated silica particles, such as by fuming or co-fuming with silanes or siloxanes. The silica particles may be produced utilizing techniques known to those skilled in the art. The production of a fumed metal oxide is a well-documented process which involves the hydrolysis of suitable feed stock vapor (such as silicon tetrachloride) in a flame of hydrogen and oxygen. Molten particles of roughly spherical shape are formed, and the particle diameters may be varied through control of process parameters. These molten spheres, referred to as primary particles, fuse with one another by undergoing collisions at their contact points to form branched, three dimensional chain-like aggregates. The formation of the aggregates is considered to be irreversible as a result of the fusion between the primary particles. During cooling and collecting, the aggregates undergo further collisions that may result in some mechanical entanglements to form agglomerates. These agglomerates are thought to be loosely held together by van der Waals forces and can be reversed, i.e. de-agglomerated, by proper dispersion in a suitable media. Mixed or co-fumed silica particles may also be produced utilizing conventional techniques known to those skilled in the art. The silica particles described herein may include other oxides such as those of aluminum, titanium, zirconium, iron, niobium, vanadium, tungsten, tin, or germanium. Such aggregates may be formed by introducing appropriate feed stocks (e.g. chloride compounds) into a flame in conjunction with an appropriate fumed silica feed stock. A non-limiting example of fumed silica particles includes AEROSIL® fumed silica available from Evonik Corporation.

Treatment of silicon dioxide particles refers to the chemical modification of the surface silanol functionality. As covered extensively in literature, there are many mechanisms that allow for surface modification via various chemical reaction routes and processes. When discussing treated silica particles it is important to understand not only the physical properties but to also understand the chemical structure at the surface. This can be seen in effect with AEROSIL® R 805 (octylsilane treated) with a 150 $m^2/g$ (+/−25) BET surface area and a pH of 3.5 to 5.5; AEROSIL® R 812 (hexamethyl disilazane treated) with a 260 $m^2/g$ (+/−30) BET surface area and a pH of 5.5 to 7.5; and AEROSIL® R 816 (hexadecylsilane treated) with a 190 $m^2/g$ (+/−20) BET surface area and a pH of 4.0 to 5.5 which create a unique balance between hydrophilic (silanol functionality) and hydrophobic (treated chemical functionality) properties.

Chemical selectivity with actives is also influenced by the degree of chemical modification at the particle's surface. One example of this can be seen between AEROSIL® R 812 and 812S (treated with hexamethyl disilazane). Both products have identical treatments however the degree of silanol group substitution is less with AEROSIL® R 812. This can shift how particles interact within a given matrix. These chemical differences in conjunction with the previously described physicochemical properties form the foundation for specific interactions between inorganic and organic components within applications.

In exemplary embodiments, the treated silica particles may have a BET surface area (ASTM D6556-07) of about 35 $m^2/g$ to about 700 $m^2/g$, for example, greater than about 60 $m^2/g$, greater than about 80 $m^2/g$, greater than about 130 $m^2/g$, or greater than about 150 $m^2/g$; less than about 400 $m^2/g$, less than about 290 $m^2/g$, less than about 250 $m^2/g$; or about 200 $m^2/g$.

In an exemplary embodiment, the sorbent carrier includes a mixture of silica particles having different degrees of hydrophobicity. For example, the sorbent carrier may include a first portion of hydrophobic silica particles and a second portion of hydrophobic silica particles that is less hydrophobic than the first portion. In an exemplary embodiment, the ratio of more hydrophobic particles to less hydrophobic particles is no more than 50:50, such as less than about 33:66, such as about 25:75. Of course, the ratio of more hydrophobic particles to less hydrophobic particles can be varied to deliver a desired release of the sorbed detergent component in the highly alkaline wash environment while inhibiting early non-desired release of the sorbed detergent component. Such ratios may range from 1:10 to 10:1, for example.

Surprisingly, it has been found that such a mixture of hydrophobic particles provides an increase release of the sorbed detergent component when introduced in a highly alkaline environment such as that of a laundry wash environment, while inhibiting release of the sorbed detergent component in wet agitated conditions, such as during use as applied with an antiperspirant.

In another embodiment, an increased release of the sorbed detergent component was obtained, along with inhibited early release such as during use in application with an antiperspirant, by first loading less hydrophobic silica particles with the sorbed component and then by treating the loaded silica particles to provide them with a more hydrophobic coating. For example, less hydrophobic silica particles may sorb the aqueous detergent components and then be treated with more hydrophobic silica particles in a ratio of about 9:1.

In a non-limiting example, each treated particle may be porous, containing an inner portion and an outer coating, with the inner portion being less hydrophobic than the outer coating. The aqueous component is sorbed by the inner portion of the sorbent carrier. In other words, as a result of the post-loading treatment, the silica particles may be considered to have a less hydrophobic inner portion and a more hydrophobic outer coating. Such an arrangement provides for increased resistance to early release of the sorbed detergent composition while providing for sufficient release in the alkaline wash environment.

The following is an example of a detergent composition in accordance with an exemplary embodiment. The example is provided for illustration purposes only and is not meant to limit the various embodiments of the detergent composition in any way. All materials are set forth in weight percent.

| EXAMPLE 1 - Detergent Composition | |
|---|---|
| Ingredient | Wt % |
| Surfactant (e.g., caprylyl/capryl glucoside) (65% Active) | 5.0 to 15.0 |
| Phosphoric acid (15% Active) | 5.0 to 15.0 |
| Gluconic acid (50% Active) | 2.0 to 10.0 |
| Malic acid | 10.0 to 20.0 |
| Citric acid | 20.0 to 30.0 |
| Citrate (e.g., sodium dihydrogen citrate) | 0.0 to 15.0 |
| Water | 5.0 to 15.0 |
| Silica | 30.0 to 40.0 |
| Total | 100.0 |

As indicated above, the detergent composition may be dispersed in a personal care product. In exemplary embodiments, the detergent composition is dispersed in an antiperspirant or deodorant. Antiperspirants and deodorants are often provided in the form of invisible solids, aerosol sprays, roll-ons, clear sticks, gels, and solid emulsions. The following examples are provided for each of these product forms and include 4 anhydrous suspensions and 2 water/oil emulsions. The emulsions are formulated to have the detergent composition in the oil phase.

The following is an example of an invisible solid antiperspirant product in accordance with an exemplary embodiment. The example is provided for illustration purposes only and is not meant to limit the various embodiments of the personal care product in any way. All materials are set forth in weight percent.

| EXAMPLE 2 - Invisible Solid Antiperspirant Product | |
|---|---|
| Ingredient | Wt % |
| Cyclopentasiloxane | 25.0 to 46.0 |
| Stearyl alcohol | 15.0 to 24.0 |
| Cetyl alcohol | 0.0 to 3.0 |
| Aluminum zirconium trichlorohydrex - GLY | 5.0 to 25.0 |
| PPG-14 butyl ether | 7.0 to 15.0 |
| Hydrogenated castor oil | 1.0 to 8.0 |
| Myristal myristate | 1.0 to 8.0 |
| Polyethylene | 0.1 to 1.5 |
| Silica | 0 to 6.0 |
| Silica dimethyl silylate | 0 to 6.0 |
| Parfum | 0.1 to 6.0 |
| Detergent Composition | 0.1 to 10.0 |
| Total | 100.0 |

The following is an example of an aerosol spray product in accordance with an exemplary embodiment. The example is provided for illustration purposes only and is not meant to limit the various embodiments of the personal care product in any way. All materials are set forth in weight percent.

| EXAMPLE 3 - Aerosol Spray Product | |
|---|---|
| Ingredient | Wt % |
| Butane | 30.0 to 45.0 |
| Cyclomethicone | 20.0 to 35.0 |
| Hydrofluorocarbon 152 | 10.0 to 25.0 |
| Aluminum chlorohydrate | 5.0 to 25.0 |
| Talc | 0.5 to 4.0 |
| Silica dimethyl silylate | 0.5 to 4.0 |
| Fragrance | 0.5 to 2.0 |
| Silica | 0.1 to 1.0 |
| Detergent Composition | 0.1 to 10.0 |
| Total | 100.0 |

The following is an example of a roll on product in accordance with an exemplary embodiment. The example is provided for illustration purposes only and is not meant to limit the various embodiments of the personal care product in any way. All materials are set forth in weight percent.

| EXAMPLE 4 - Roll on Product | |
|---|---|
| Ingredient | Wt % |
| Aluminum zirconium pentachlorohydrex - GLY | 5.0 to 25.0 |
| Cyclomethicone | 40.0 to 80.0 |
| Disteardimonium hectorite | 1.0 to 10.0 |
| Tocopheryl acetate | 0.1 to 3.0 |
| Propylene carbonate | 0.1 to 3.0 |
| Fragrance | 0.1 to 3.0 |
| Detergent Composition | 0.1 to 10.0 |
| Total | 100.0 |

The following is an example of a clear stick product in accordance with an exemplary embodiment. The example is provided for illustration purposes only and is not meant to limit the various embodiments of the personal care product in any way. All materials are set forth in weight percent.

| EXAMPLE 5 - Clear Stick Product | |
|---|---|
| Ingredient | Wt % |
| Propylene glycol | 50.0 to 95.0 |
| Aluminum zirconium tetrachlorohydrex - GLY | 5.0 to 25.0 |

-continued

EXAMPLE 5 - Clear Stick Product

| Ingredient | Wt % |
| --- | --- |
| Hydroxypropyl cellulose | 0.1 to 5.0 |
| Tetrasodium EDTA | 0.1 to 5.0 |
| Dibenzylidene sorbitol | 0.1 to 5.0 |
| Diisopropyl sebacate | 0.1 to 5.0 |
| Fragrance | 0.1 to 3.0 |
| PEG/PPG-14/4 dimethicone | 0.1 to 5.0 |
| Detergent Composition | 0.1 to 10.0 |
| Total | 100.0 |

The following is an example of a gel product in accordance with an exemplary embodiment. The example is provided for illustration purposes only and is not meant to limit the various embodiments of the personal care product in any way. All materials are set forth in weight percent.

EXAMPLE 6 - Gel Product

| Ingredient | Wt % |
| --- | --- |
| Water | 20.0 to 50.0 |
| Aluminum zirconium octachlorohydrex GLY | 5.0 to 25.0 |
| Ethanol | 5.0 to 15.0 |
| Cyclomethicone | 1.0 to 12.0 |
| PEG/PPG-18/28 dimethicone | 1.0 to 12.0 |
| Propylene glycol | 1.0 to 12.0 |
| Fragrance | 0.1 to 3.0 |
| Detergent Composition | 0.1 to 10.0 |
| Total | 100.0 |

The following is an example of a solid emulsion product in accordance with an exemplary embodiment. The example is provided for illustration purposes only and is not meant to limit the various embodiments of the personal care product in any way. All materials are set forth in weight percent.

EXAMPLE 7 - Solid Emulsion Product

| Ingredient | Wt % |
| --- | --- |
| Water | 20.0 to 50.0 |
| Aluminum zirconium octachlorohydrex GLY | 5.0 to 25.0 |
| Cyclohexasiloxane | 5.0 to 15.0 |
| Polyethylene | 5.0 to 15.0 |
| C12-15 alkyl benzoate | 5.0 to 15.0 |
| PEG-8 | 2.0 to 10.0 |
| PPG-17 | 2.0 to 10.0 |
| Cetyl PEG/PPG-10/1 dimethicone | 1.0 to 5.0 |
| Fragrance | 0.1 to 3.0 |
| Detergent Composition | 0.1 to 10.0 |
| Total | 100.0 |

As indicated in the examples above, each antiperspirant product contains at least one active ingredient or active antiperspirant compound, which typically includes metal salts. The metal salts are believed to reduce perspiration by diffusing through the sweat ducts of eccrine glands and apocrine glands and hydrolyzing in the sweat ducts. They combine with proteins to form an amorphous metal hydroxide agglomerate that plugs the sweat ducts so that perspiration cannot diffuse to the skin surface. Some active antiperspirant compounds that may be used include astringent metallic salts, such as inorganic and organic salts of aluminum, zirconium, and zinc, as well as mixtures thereof. Some examples are aluminum-containing and/or zirconium-containing salts or materials, such as aluminum halides, aluminum chlorohydrates, aluminum hydroxyhalides, zirconyl oxyhalides, zirconyl hydroxyhalides, and mixtures thereof. Exemplary aluminum salts include those having the general formula $Al_2(OH)_aCl_b$ masking layer ($H_2O$), wherein a is from 2 to about 5; the sum of a and b is about 6; masking layer is from about 1 to about 6; and wherein a, b, and masking layer may have non-integer values. Exemplary zirconium salts include those having the general formula $ZrO(OH)_{2-a}Cl_a$ masking layer ($H_2O$), wherein a is from about 1.5 to about 1.87, masking layer is from about 1 to about 7, and wherein a and masking layer may both have non-integer values. Some zirconium salt examples are those complexes that additionally contain aluminum and glycine, commonly known as ZAG complexes. These ZAG complexes contain aluminum chlorohydroxide and zironyl hydroxy chloride conforming to the above-described formulas. Examples of active antiperspirant compounds suitable for use in the various embodiments contemplated herein include aluminum dichlorohydrate, aluminum-zirconium octachlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum-zirconium trichlorohydrate, aluminum zirconium tetrachlorohydrate, aluminum zirconium pentachlorohydrate, aluminum zirconium octachlorohydrate, aluminum zirconium trichlorohydrex glycine complex, aluminum zirconium tetrachlorohydrex glycine complex, aluminum zirconium pentachlorohydrex glycine complex, aluminum zirconium octachlorohydrex glycine complex, zirconium chlorohydrate, aluminum chloride, aluminum sulfate buffered, and the like, and mixtures thereof.

The active antiperspirant compound is preferably in a perspiration-reducing effective amount. In one embodiment, the antiperspirant composition comprises an active antiperspirant compound present in the amount of from about 5 to about 30 weight percent. As used herein, weight percent or wt % of an antiperspirant salt is calculated as anhydrous weight percent in accordance with the U.S.P. method, as is known in the art. This calculation excludes any bound water and glycine.

In certain embodiments, the antiperspirant product includes an anhydrous, hydrophobic vehicle, which includes a volatile silicone and/or a high melting component. In an exemplary embodiment, the active antiperspirant compound is suspended in the anhydrous, hydrophobic vehicle.

For use as an antiperspirant stick, the high melting components may include any suitable material that melts at a temperature of about 70° C. or higher. Typical of such materials are the high melting point waxes. These include beeswax, spermaceti, carnauba, bayberry, candelilla, montan, ozokerite, ceresin, paraffin waxes, semi-microcrystalline and microcrystalline waxes, hydrogenated jojoba oil, and hydrogenated castor oil (castor wax). Other suitable high melting components include various types of high melting gelling agents such as polyethylene-vinyl acetate copolymers, polyethylene homopolymers, 12-hydroxystearic acid, and substituted and unsubstituted dibenzylidene alditols. Typically, the high melting components comprise about 1 to about 25 wt %, such as from about 2 to about 15 wt %, of the antiperspirant composition. Volatile silicones include cyclomethicones and dimethicones, discussed above.

Other components may include, for example, non-volatile silicones, polyhydric alcohols having 3-6 carbon atoms and 2-6 hydroxy groups, fatty alcohols having from 12 to 24 carbon atoms, fatty alcohol esters, fatty acid esters, fatty amides, non-volatile paraffinic hydrocarbons, polyethylene glycols, polypropylene glycols, polyethylene and/or polypropylene glycol ethers of $C_4$-$C_{20}$ alcohols, polyethylene and/or polypropylene glycol esters of fatty acids, and mixtures thereof.

Non-volatile silicones include polyalkylsiloxanes, polyalkylaryl siloxanes, and polyethersiloxanes with viscosities of about 5 to about 100,000 centistokes at 25° C., polymethylphenylsiloxanes with viscosities of about 15 to about 65 centistokes, and polyoxyalkylene ether dimethylsiloxane copolymers with viscosities of about 1200 to about 1500 centistokes.

Useful polyhydric alcohols include propylene glycol, butylenes glycol, dipropylene glycol and hexylene glycol. Fatty alcohols include stearyl alcohol, cetyl alcohol, myristyl alcohol, oleyl alcohol, and lauryl alcohol. Fatty alcohol esters include $C_{12-15}$ alcohols benzoate, myristyl lactate, cetyl acetate, and myristyl octanoate. Fatty acid esters include isopropyl palmitate, myristyl myristate, and glyceryl monostearate. Fatty amides include stearamide MEA, stearamide MEA-stearate, lauramide DEA, and myristamide MIPA.

Non-volatile paraffinic hydrocarbons include mineral oils and branched chain hydrocarbons with about 16 to 68, preferably about 20 to 40, carbon atoms. Suitable polyethylene glycols and polypropylene glycols will typically have molecular weights of about 500 to 6000, such as PEG-10, PEG-40, PEG-150 and PPG-20, often added as rheology modifiers to alter product appearance or sensory attributes.

Polyethylene and/or polypropylene glycol ethers or $C_4$-$C_{20}$ alcohols include PPG-10 butanediol, PPG-14 butyl ether, PPG-5-buteth-7, PPG-3-isostearth-9, PPG-3-myreth-3, oleth-10, and steareth-20. Polyethylene and/or polypropylene glycol esters of fatty acids include PEG-8 distearate, PEG-10 dioleate, and PPG-26 oleate. These are generally added to give emollient properties.

The antiperspirant product contemplated herein also may comprise additives, such as those used in conventional antiperspirants. For example, in addition to antiperspirant efficacy, the antiperspirant composition may comprise additives that cause the antiperspirant composition to exhibit long-lasting fragrance, odor protection, bacteria control, and/or another desired purpose and/or function. These additives include, but are not limited to, fragrances, including encapsulated fragrances, dyes, pigments, preservatives, antioxidants, moisturizers, and the like. These optional ingredients can be included in an amount of from about 0 to about 20 wt % of the antiperspirant composition.

The above list of materials is by way of example only and is not intended to be a comprehensive list of all potential components of the antiperspirant products contemplated herein. Other high and low melting waxes, volatile and non-volatile compounds and other suitable components are readily identifiable to those skilled in the art. Of course, other ingredients such as particulate polyolefins, talcum materials, colorants and preservatives may also be included as desired. For example, the antiperspirant composition may include up to about 5% fragrance or about 2% colorant by weight.

In accordance with exemplary embodiments, a method for making the detergent composition includes mixing water, acid and surfactant to form the aqueous detergent component. The aqueous detergent component has a pH of less than 2, such as less than 1. The aqueous detergent composition remains flowable despite its high acid content. Further, the method may include mixing acid salts, such as citrates, into the aqueous detergent composition.

After the aqueous detergent composition is prepared, it may be sorbed by the sorbent carrier. As explained above, the sorbent carrier may comprise hydrophobic silica particles having a substantially uniform hydrophobicity, or two or more portions of hydrophobic silica particles having different levels of hydrophobicity. After sorbing the aqueous detergent composition with the sorbent carrier, the detergent composition may be dispersed into a personal care product. Suitable methods for forming the personal care product known to those skilled in the art may be used.

In certain embodiments, after sorbing the aqueous detergent composition with the sorbent carrier a second hydrophobicity treatment is performed. Specifically, the loaded hydrophobic particles are post-treated with particles having higher hydrophobicity. As a result, the loaded silica particles are imparted with a coating having higher hydrophobicity. The internal portion of the loaded silica particles retains its lower hydrophobic level.

Accordingly, detergent compositions and detergent compositions dispersed in personal care products, such as antiperspirant products, have been disclosed. Further, detergent compositions that provide for sorbing aqueous detergent components on hydrophobic particles for selected release in an alkaline environment have been described. The aqueous detergent components described may be highly acidic, with a pH of less than 2 or less than 1. Further, the sorbent carrier may include mixtures of particles having different levels of hydrophobicity or include particles which have a lower internal hydrophobicity and an outer coating with a higher hydrophobicity.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the processes without departing from the scope defined by the claims, which includes known equivalents and foreseeable equivalents at the time of filing this patent application.

What is claimed is:

1. A detergent composition comprising:
   a) from 30.0 to 40.0 wt % sorbent carrier comprising hydrophobic silica;
   b) from 0.1 to 15% of an acid precursor comprising citrate;
   c) a sorbed component comprising by weight of the detergent composition:
      i) from 5 to 15% surfactant;
      ii) from 5 to 15% phosphoric acid;
      iii) from 2 to 10% gluconic acid;
      iv) from 10 to 20% malic acid;
      v) from 20 to 30% citric acid; and
      vi) from 5 to 15% water;
      wherein the sorbed component is sorbed by the sorbent carrier.

2. The detergent composition of claim 1 wherein the sorbent carrier comprises particles and wherein the particles are dispersed in a personal care product.

3. The detergent composition of claim 1 wherein the citrate is sodium dihydrogen citrate.

4. The detergent composition of claim 1 wherein the surfactant is caprylyl/capryl glucoside.

5. The detergent composition of claim 4 wherein the sorbed component is in aqueous form.

6. The detergent composition of claim 1 wherein the sorbed component has a pH of less than about 3.5.

7. The detergent composition of claim 1 wherein the sorbed component has a pH of less than about 2.

8. The detergent composition of claim 1 wherein the sorbent carrier comprises a mixture of hydrophobic silica particles comprising a first portion and a second portion, wherein the second portion is less hydrophobic than the first portion.

9. The detergent composition of claim 1 wherein the sorbent carrier comprises porous hydrophobic silica particles, wherein each silica particle has an inner portion and an outer coating, and wherein the inner portion is less hydrophobic than the outer coating.

10. The detergent composition of claim 1 wherein the sorbent carrier is configured to at least partially dissolve in an alkaline environment with a pH greater than about 9 and to release the sorbed component.

11. A detergent composition comprising:
   a) an aqueous component comprising by weight of the detergent composition:
      i) from 5 to 15% surfactant;
      ii) from 5 to 15% phosphoric acid;
      iii) from 32 to 70% alpha hydroxy acid; and
      iv) from 5 to 25% water;
      wherein the aqueous component has a pH less than about 1; and
   b) from 30.0 to 40.0 wt % sorbent carrier comprising hydrophobic silica, wherein the aqueous component is sorbed by the sorbent carrier.

12. The detergent composition of claim 11 wherein the sorbent carrier comprises a mixture of hydrophobic silica particles comprising a first portion and a second portion, wherein the second portion is less hydrophobic than the first portion.

13. The detergent composition of claim 11 wherein the sorbent carrier comprises porous hydrophobic silica particles, wherein each silica particle has an inner portion and an outer coating, and wherein the inner portion is less hydrophobic than the outer coating.

14. The detergent composition of claim 11 wherein the sorbent carrier is configured to dissolve or partially dissolve in an alkaline environment with a pH greater than about 9 and to release the aqueous component.

15. The detergent composition of claim 11 wherein the sorbent carrier comprises particles and wherein the particles are dispersed in a personal care product.

16. A detergent composition dispersed in a personal care product and comprising:
   a) an aqueous component comprising by weight of the detergent composition:
      i) from 5 to 15% surfactant;
      ii) from 37 to 75% acid;
      iii) from 5 to 25% water; and
   b) from 30.0 to 40.0 wt % sorbent carrier comprising hydrophobic silica particles, wherein each particle has an inner portion and an outer coating, wherein the inner portion is less hydrophobic than the outer coating, and wherein the aqueous component is sorbed by the inner portion of the sorbent carrier.

17. The detergent composition of claim 16 wherein each portion of the sorbent carrier is configured to dissolve in an alkaline environment with a pH greater than about 9 and to release the sorbed component.

* * * * *